United States Patent [19]
Smith

[11] Patent Number: 5,817,095
[45] Date of Patent: Oct. 6, 1998

[54] UNDERCUTTING SURGICAL INSTRUMENT

[75] Inventor: Graham Smith, Plaistow, N.H.

[73] Assignee: Smith & Nephew, Inc., Andover, Mass.

[21] Appl. No.: 604,873

[22] Filed: Feb. 22, 1996

[51] Int. Cl.[6] .................................................. A61B 17/00
[52] U.S. Cl. ............................................. 606/79; 408/159
[58] Field of Search ..................... 606/1, 79–81, 606/159, 170, 180; 408/159, 187, 188; 128/750–755, 898

[56] References Cited

U.S. PATENT DOCUMENTS

| | | |
|---|---|---|
| 3,692,020 | 9/1972 | Schied . |
| 4,142,517 | 3/1979 | Stavropoulos et al. . |
| 4,274,414 | 6/1981 | Johnson et al. . |
| 4,307,636 | 12/1981 | Lacey . |
| 4,347,768 | 9/1982 | Boehm . |
| 4,357,846 | 11/1982 | Primo ........................................ 408/159 |
| 4,362,161 | 12/1982 | Reimels et al. . |
| 4,461,305 | 7/1984 | Cibley . |
| 4,529,022 | 7/1985 | Jacobson . |
| 4,738,255 | 4/1988 | Goble et al. . |
| 4,926,877 | 5/1990 | Bookwalter . |
| 4,992,010 | 2/1991 | Fischer ...................................... 408/159 |
| 5,062,845 | 11/1991 | Kuslich et al. . |
| 5,197,967 | 3/1993 | Wilson . |
| 5,224,949 | 7/1993 | Gomringer et al. ..................... 606/159 |
| 5,242,461 | 9/1993 | Kortenbach et al. .................... 606/159 |
| 5,269,785 | 12/1993 | Bonutti . |
| 5,324,300 | 6/1994 | Elias et al. . |
| 5,366,468 | 11/1994 | Fucci et al. . |

*Primary Examiner*—Michael Buiz
*Assistant Examiner*—William Lewis
*Attorney, Agent, or Firm*—Fish & Richardson P.C.

[57] ABSTRACT

An undercutting surgical instrument comprises a housing disposed along a longitudinal axis between a proximal region and a distal section which is sized to be inserted into a hole in a bone. A passage with an open end at the distal section is disposed through the housing along an axis to receive a guide wire for positioning the distal section adjacent to the bone. A plurality of axially extending slots in walls of the housing are arranged around the passage and extend between the proximal region and the distal section of the housing, and receive a plurality of axially extending arms. A proximal region of each arm is pivotally mounted to the housing, and a distal end of each arm carries a cutting tool so that the cutting tools are arranged around the open end of the passage (and the guide wire). An actuator is movably disposed within the passage and coupled to selectively pivot the arms transversely to the axis so that the cutting tools are moved between a retracted position (in the slots) and a deployed position (in which the cutting tools protrude from the slots). The actuator is also rotatably coupled to the housing to rotate the distal section and the deployed cutting tools to form an undercut in the bone hole around the guide wire. The instrument is highly effective in forming an undercut hole shaped to securely receive a tissue plug, such as a cartilage plug, during procedures to repair the articular cartilage of a joint. The undercut receives a lip on the tissue plug, and thus holds the plug in the hole without requiring external anchoring (e.g., suture or pins).

21 Claims, 8 Drawing Sheets

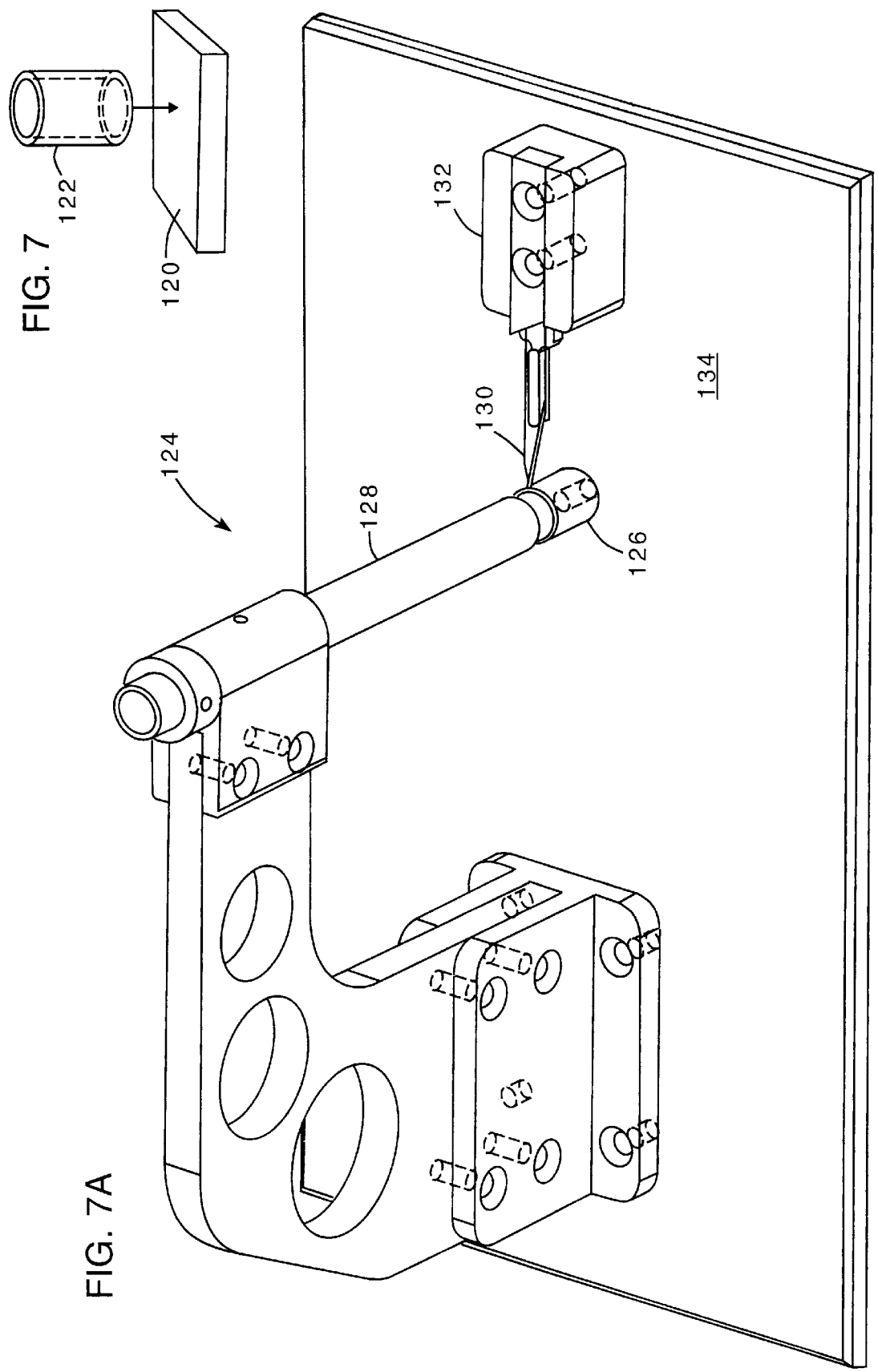

UNDERCUTTING SURGICAL INSTRUMENT

BACKGROUND OF THE INVENTION

This invention relates to forming a hole in bone tissue during surgery.

One application in which a bone hole is formed is to provided a fixation site for a suture anchor during surgery to repair ligaments in the knee, shoulder, and other joints. Typically, the hole is drilled by either a pointed or flat-bottomed cylindrical drill bit. The drill bit usually is cannulated for insertion over a Kirshner wire (called a "K-wire"), which helps ensure that the hole is correctly oriented. After the drill bit, bone debris, and K-wire are removed, the suture anchor is inserted and secured within the hole.

SUMMARY OF THE INVENTION

This invention features a surgical instrument for making an undercut in a bone hole. Among other uses, the undercutting surgical instrument is highly effective in forming a hole shaped to securely receive a tissue plug, such as a cartilage plug, during procedures to repair the articular cartilage of a joint. The undercut receives a lip on the tissue plug, and thus holds the plug in the hole without requiring external fixation (e.g., by suture or with a pin).

In one general aspect, the surgical instrument comprises a housing having a distal section sized to be inserted into the bone hole and a passage therethrough sized to receive a guide wire for placing the distal section at a selected location at the bone; an arm which is pivotally mounted to the housing adjacent to the passage and carries a cutting tool at the distal section is selectively pivoted by an actuator to move the cutting tool between a retracted position and a deployed position, and the actuator rotates the distal section with the cutting tool in the deployed position so that the cutting tool forms an undercut in the bone hole around the guide wire.

Preferred embodiments include the following features.

The cutting tool is biased to the retracted position. This helps ensure that the tool is not deployed prematurely and is particularly useful when the instrument is used to form an undercut in a pre-drilled hole.

Preferably, the instrument includes multiple, pivotally mounted arms arranged around the passage, and each of the arms carries a cutting tool at the distal section of the housing. The actuator selectively pivots all of the arms to move the cutting tools between the retracted and deployed positions for cutting. When the actuator rotates the distal section, the deployed cutting tools form the undercut in the bone hole around the guide wire.

The arm (or arms) is disposed generally along an axis between a proximal region, at which the arm is pivotally mounted to the housing, and a distal end at which the arm carries the cutting tool. The arm is pivotally mounted within an axial slot in the housing so that cutting tool is disposed in the slot when in the retracted position and protrudes transversely from said slot when moved to the deployed position by the actuator.

The actuator is disposed within the passage and is axially movable with respect to the housing to selectively pivot the arm. In one embodiment, the arm includes an axially disposed camming surface positioned to be engaged by the actuator so that the axial movement of the actuator toward the distal section pivots the arm transversely and moves the cutting tool between the retracted and deployed positions.

The actuator preferably is spring biased axially away from the distal section. This helps avoid unwanted deployment of the cutting tool.

Preferably, the actuator includes a transversely disposed pin that engages the arm's camming surface. More specifically, the housing includes an axially elongated aperture adjacent to the camming surface, and the pin extends through the aperture to engage the camming surface. The engagement of the pin in the aperture also serves to rotatably couple the actuator to the housing so that rotation of said actuator is transmitted to rotate the distal section and the cutting tool. The actuator and the pin include openings which communicate with the passage to receive the guide wire.

The surgical instrument is simple in construction, easy to use, and provides the surgeon with a way of accurately forming an undercut bone hole. The cannulated construction of the instrument allows the surgeon to position the instrument against the bone using the guide wire (e.g., a K-wire). As a result, the undercut hole will be more precisely located than if the surgeon were required to position the instrument freehand.

The invention also features a procedure for installing a tissue plug into bone tissue. In one general aspect, a hole having an undercut is formed in the bone tissue, and a tissue plug having a portion configured to be received in the undercut is inserted in the hole so that the portion of the plug is disposed in the undercut.

The engagement of the plug in the undercut securely holds the plug in place while the tissues bond together. Accordingly the need for external devices such as suture or pins to temporarily hold the plug in the hole is eliminated. Among other advantages is a decrease in healing time and patient discomfort. Moreover, because the plug need not be pierced (e.g., with suture or a pin) to hold it in the hole, the risk of subsequent infection or damage is reduced.

Preferred embodiments include the following features.

The hole is formed in the bone, and the undercut is then formed in the hole (e.g., using the above-described surgical instrument). The undercut is annular, and an annular lip is provided on the tissue plug. The complementary shapes of the undercut and the lip further enhances retention of the plug. After the tissue plug is inserted, the plug is contoured so that an exposed surface of the tissue plug is flush with surrounding tissue.

Also featured by the invention is a method for forming the tissue plug. In one aspect, the plug is cut from a tissue sample, and a protrusion having a selected configuration is formed on a surface of the plug.

In a preferred embodiment, the plug is cylindrical, and the protrusion is annular.

The plug is highly useful in the surgical procedure discussed above. As mentioned, the protrusion on the plug provides a way of securing the plug within an undercut hole without requiring suture or the like.

Other features and advantages of the invention will be apparent from the following detailed description, and from the claims.

BRIEF DESCRIPTION OF THE DRAWING

FIGS. 7–7A show instruments for forming the cartilage plug of FIGS. 5 and 5A.

DESCRIPTION OF PREFERRED EMBODIMENTS

Figure 1:
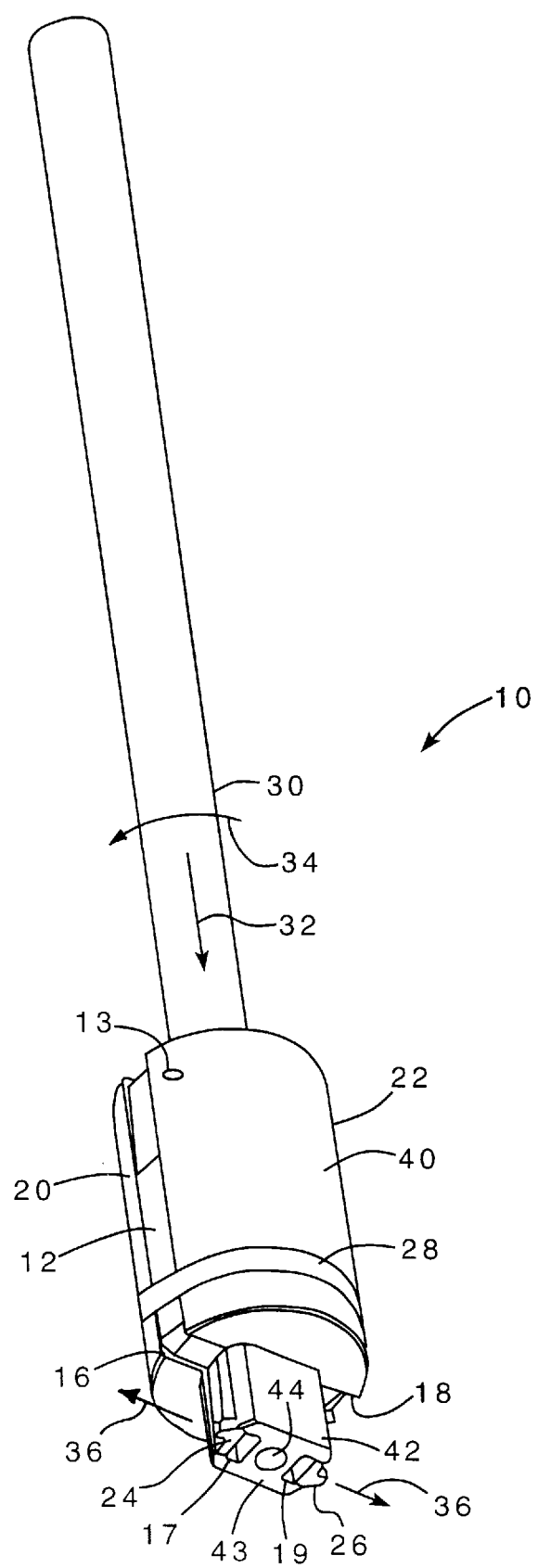
FIG. 1 shows an undercutting surgical instrument.

Referring to FIG. 1, undercutting surgical instrument 10 includes a pair of axially extending arms 12, 14 (arm 14 is not visible in FIG. 1) pivotally mounted near their proximal ends within axial slots 16, 18 in the exterior surface 20 of a housing 22. Cutting tools 24, 26, are supported at the distal ends of arms 12, 14, respectively. Arms 12, 14 are biased within slots 16, 18 by a band 28 (e.g., made from elastic or metal) that surrounds housing 22, and with arms 12, 14 so positioned cutting tools 24, 26 are captured in distal regions 17, 19 of slots 16, 18.

As described in more detail below, a hollow actuating rod 30 received within housing 22 is movable axially with respect to housing 22 to deploy cutting tools 24, 26 within a bone hole. More specifically, when actuating rod 30 is slid axially (in the direction of arrow 32), rod 30 engages arms 12, 14 distally of their pivot points, thereby urging arms 12, 14—and hence cutting tools 24, 26—radially outwardly from slots 16, 18 in the direction of arrows 36. Put another way, the axial motion of rod 30 moves cutting tools 24, 26 from a retracted position (within slots 16, 18) to the deployed position shown in FIG. 1.

As is also described below, rod 30 is linked to housing 22 so that rotational motion of rod 30 (in the direction of arrow 34) is transmitted to housing 22, and thence to arms 12, 14 and cutting tools 24, 26. Accordingly, with cutting tools 24, 26 in the deployed position shown in FIG. 1, rotating rod 30 causes cutting tools 24, 26 to produce an undercut in the bone hole.

Figure 2:
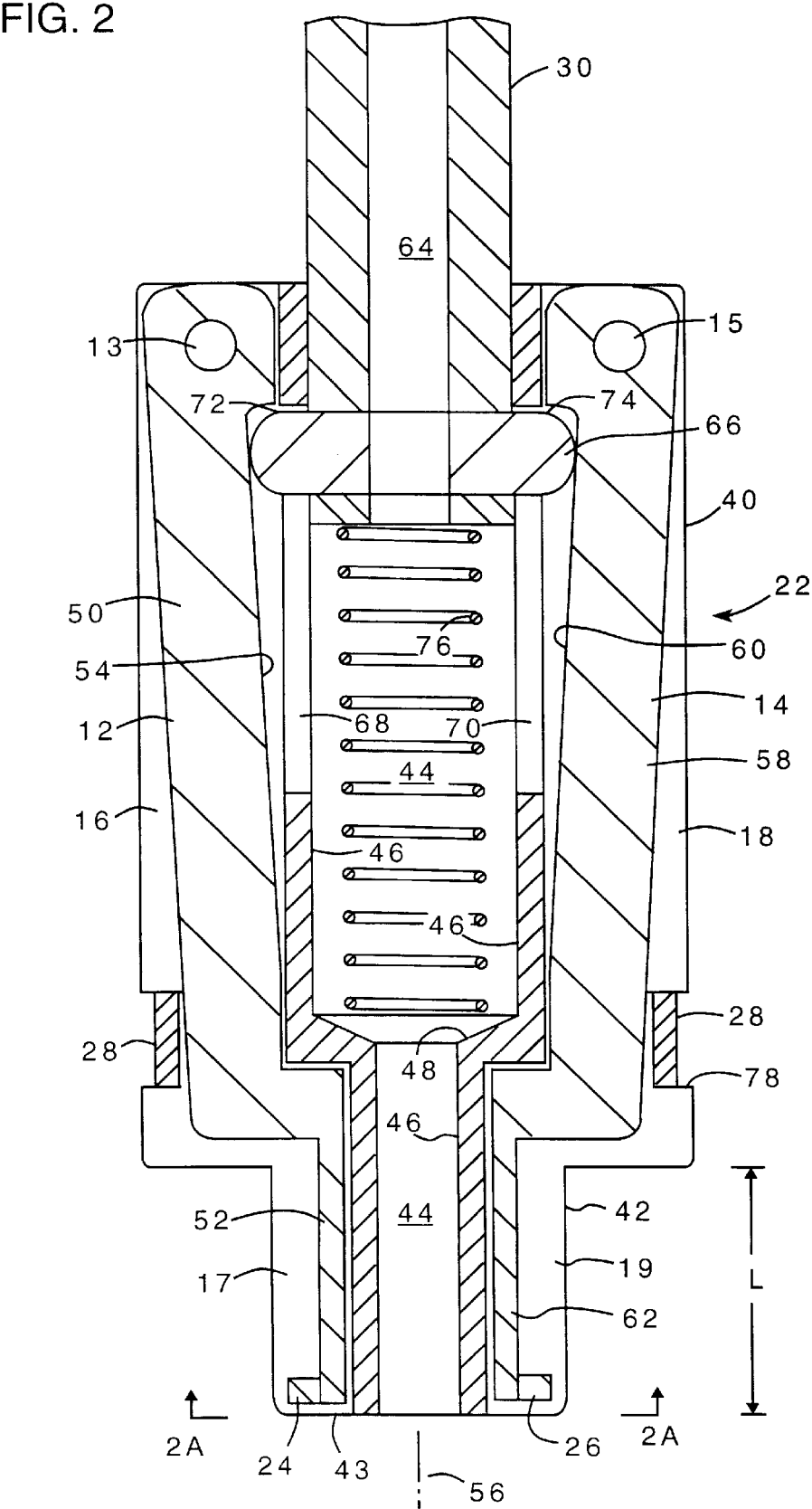
FIG. 2 is a cross-sectional side view of the surgical instrument of FIG. 1 with the cutting tools of the instrument in a retracted position.

Referring also to FIG. 2, instrument 10 is shown with arms 12, 14 positioned within slots 16, 18 (i.e., with cutting tools 24, 26 in the retracted position). Housing 22 includes a generally cylindrical body 40 which steps down in size at a hollow distal section 42 that terminates in a flat distal surface 43. As discussed in more detail below, the length L of distal section (e.g., 10 mm) corresponds to the maximum depth of the undercut to be formed using instrument 10. A generally cylindrical central passage 44 is disposed longitudinally through body 40 and distal section 42 and is defined by an axial interior wall 46 of housing 22. A radial step 48 in interior wall 46 serves to reduce the diameter of passage 44 near the distal end of body 40.

Slots 16, 18 are disposed along the entire axial length of housing 22 follow the exterior contour of body 40 and distal section 42. Thus, each slot 16, 18 "L-shaped" at the junction between body 40 and distal section 32. Arms 12, 14 are shaped to lie completely within respective slots 16, 18 when in the retracted position. For example, arm 12 includes an L-shaped proximal section 50 that fits within slot 16 along the length of body 40, and a distal section 52 that lies within distal portion 17 of slot 16. The interior axial surface 54 of proximal section 50 is tapered inwardly along the length of section 54 to define a camming surface oriented at an acute angle with the longitudinal axis 56 of instrument 10 for purposes to be described. Proximal section 50 is pivotally mounted to body 40 within slot 16 by a pin 13 located near the extreme proximal end of arm 12.

Similarly, an L-shaped proximal portion 58 of arm 14 with an inwardly-tapered interior camming surface 60 fits within slot 18 in body 40, and a distal section 62 of arm 14 is disposed within distal portion 19 of slot 18. Arm 14 is pivotally mounted to body 40 by a pin 15 located near the extreme proximal end of section 58.

Actuator rod 30 is received in the proximal end of body passage 44 along longitudinal axis 56, and includes an interior passage 64 that communicates with passage 44. Rod 30 is linked to housing 22 by a transversely extending pin 66 press fit into the distal end of rod 30. (Pin 66 includes a longitudinal hole aligned with passage 64.) Pin 66 is longer than the diameter of passage 44, and the ends of pin 66 extend through a pair of opposing, axially elongated apertures 68, 70 in wall 46 and engage the tapered interior camming surfaces 54, 60 of arms 12, 14, respectively.

The proximal ends of apertures 68, 70 are closed by surfaces 72, 74, respectively, to capture rod 30 within housing body 40. A coil spring 76 is disposed in passage 44 of body 40 between radial surface 48 and the distal end of rod 30. Spring 76 biases rod 30 proximally so that pin 66 abuts aperture proximal surfaces 72, 74, as shown in FIG. 2. With rod 30 in this position, pin 66 engages arms 12, 14 adjacent to pivot pins 13, 15 and does not urge arms 12, 14 radially outwardly to the deployed position shown in FIG. 1. Band 28 (which is disposed in a circumferential groove 78 near the distal end of body 40) encircles and applies an inwardly-directed, radial force to arms 12, 14 to help retain the arms in the retracted position shown.

Figure 2A:
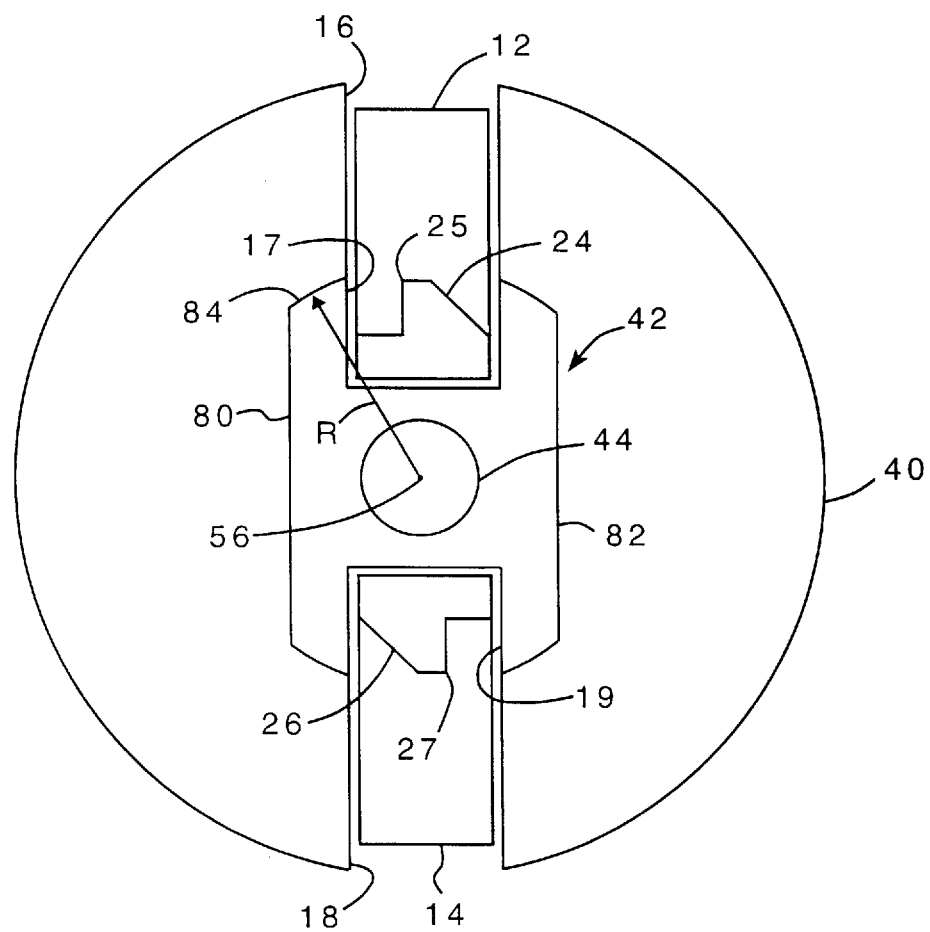
FIG. 2A is an end view of the instrument of FIG. 2, taken along lines 2A—2A.

Referring also to FIG. 2A, as seen from the distal end of surgical instrument 10, with arms 12, 14 disposed within slots 16, 18, cutting tools 24, 26 are completely retracted into the distal portions 17, 19 of slots 16, 18. That is, cutting tools 24, 26 do not protrude radially from housing distal section 32. Thus, the sharp cutting edges 25, 27 of tools 24, 26 are not exposed to tissue.

Housing distal end 42 is generally rectangular in cross section, and has a pair of parallel, straight sides 80, 82 which are oriented in the same direction as slots 16, 18. The corners 84 of distal section 42 are curved to avoid damaging the tissue when instrument 10 is operated as well as inserted into and removed from tissue. Corners 84 each have the same radius of curvature R from a point on longitudinal axis 56. Thus, corners 84 define a circle (e.g., 10 mm in diameter) that circumscribes the distal portions 17, 19 of slots 16, 18.

Figure 3:
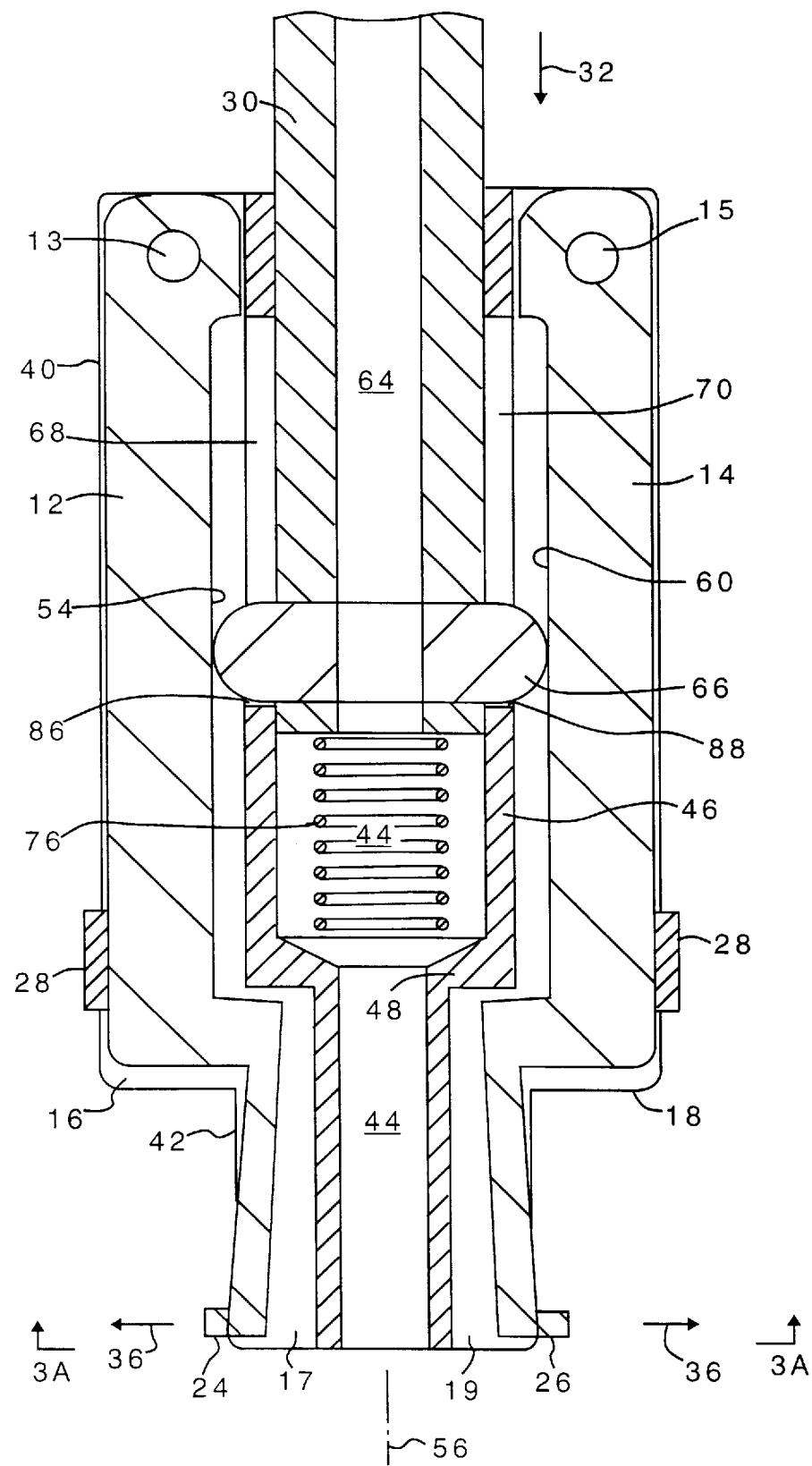
FIG. 3 is a cross-sectional side view of the surgical instrument of FIG. 1 with the cutting tools of the instrument in a deployed position.

Referring to FIG. 3, to deploy cutting tools 24, 26 from slots 16, 18, rod 30 is moved axially within body 40 in the direction of arrow 32. Pin 66 engages the tapered interior camming surfaces 54, 60 of arms 12, 14 as pin 66 travels axially within apertures 68, 70 (the ends of pin 66 are rounded to help pin 66 slide smoothly along surfaces 54, 60). Due to the inward taper of surfaces 54, 60, pin 66 pushes arms 12, 14 radially outwardly in a camming action as rod 30 moves distally. The radial forces applied by pin 66 overcome the inward biasing provided by band 28, and thus pivot arms 12, 14 swing about their respective pivot pins 13, 15 to deploy cutting tools 24, 26 from slots 16, 18 in the direction of arrows 36.

The axial travel of pin 66 is limited by the distal surfaces 86, 88 of apertures 68, 70. Spring 76, which is compressed by the axial movement of rod 30, biases rod 30 back to the position shown in FIG. 2 when the axial force is removed from rod 30. The resilience of band 28 helps return arms 12, 14 to their fully retracted position with slots 16, 18.

The engagement of pin 66 within apertures 68, 70 also rotatably couples rod 30 to housing 22. That is, when rod 30 is rotated (in the direction of arrow 34, FIG. 1), pin 66 engages the housing interior wall 46 at the sides of apertures 68, 70, thereby rotating housing 22 (and hence arms 12, 14 and cutting tools 24, 26).

Figure 3A:
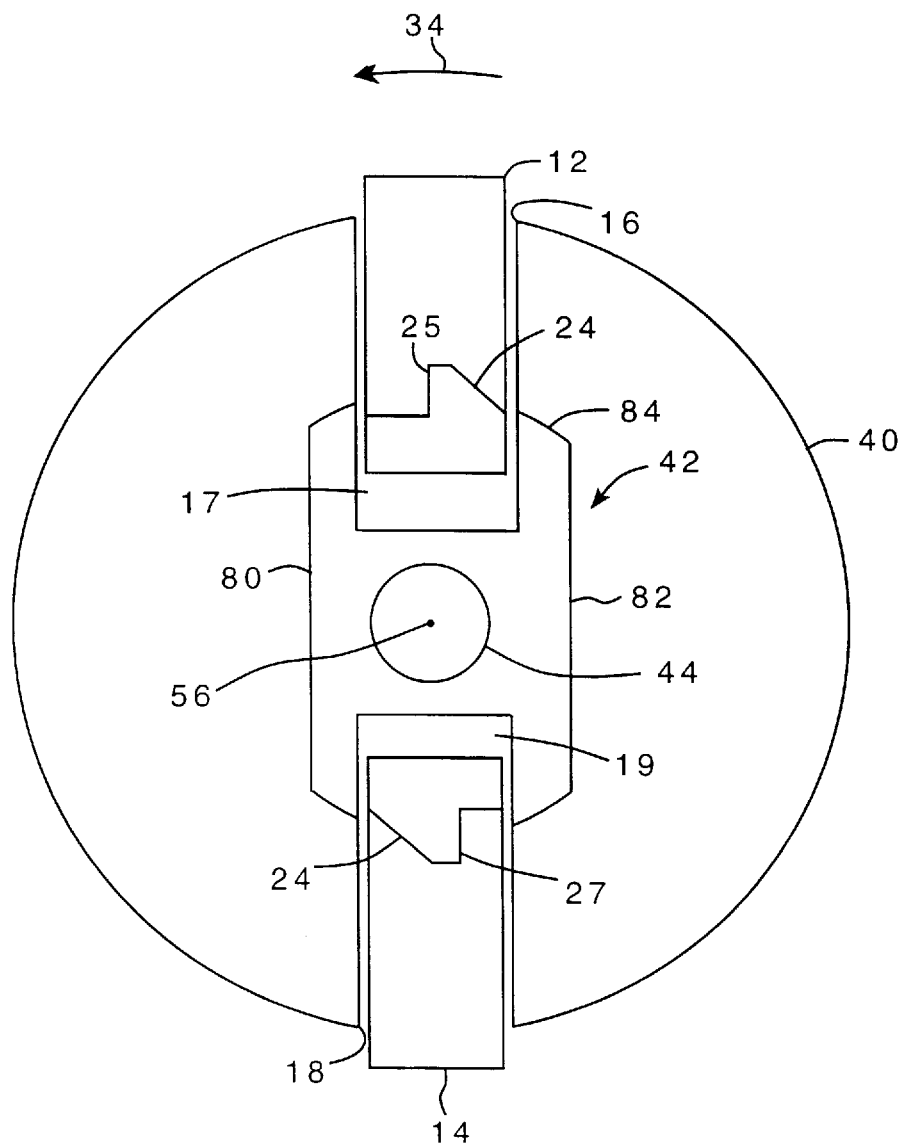
FIG. 3A is an end view of the instrument of FIG. 3, taken along lines 3A—3A.

Referring also to FIG. 3A, with cutting tools 24, 26 deployed, the sharp cutting edges 25, 27 of tools 24, 26 protrude radially from distal portions 17, 19 of slots 16, 18 and are exposed to tissue. Each cutting tool 24, 26 is approximately 1 mm in height and protrudes about 1 mm from its slot. Thus, as rod 30 is rotated in the direction of arrow 34, distal end 42 also rotates and causes cutting tools 24, 26 to cut tissue exposed thereto, thereby forming a 1 mm high, 12 mm diameter annular undercut in the bone hole.

Figure 4:
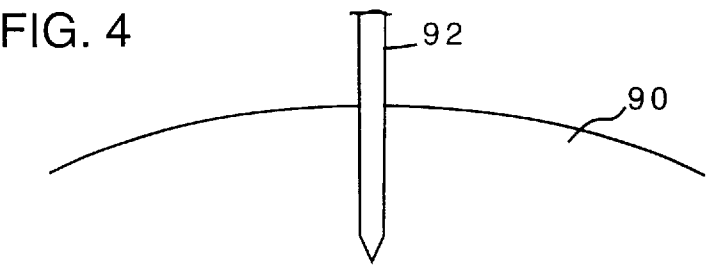
FIGS. 4–4B show illustrate the use of the surgical instrument of FIG. 1 to form an undercut hole in tissue.
Figure 4A:
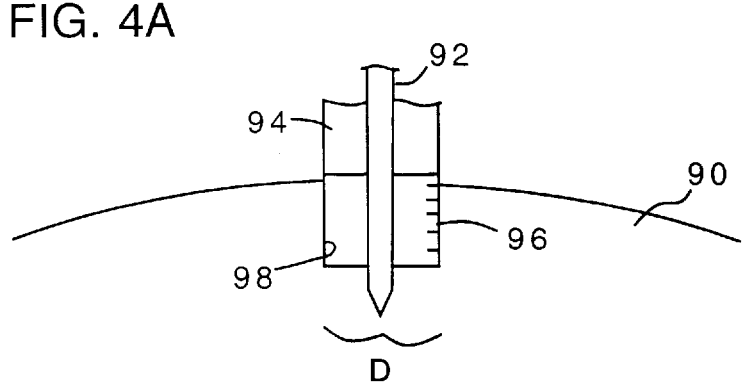
Figure 4B:
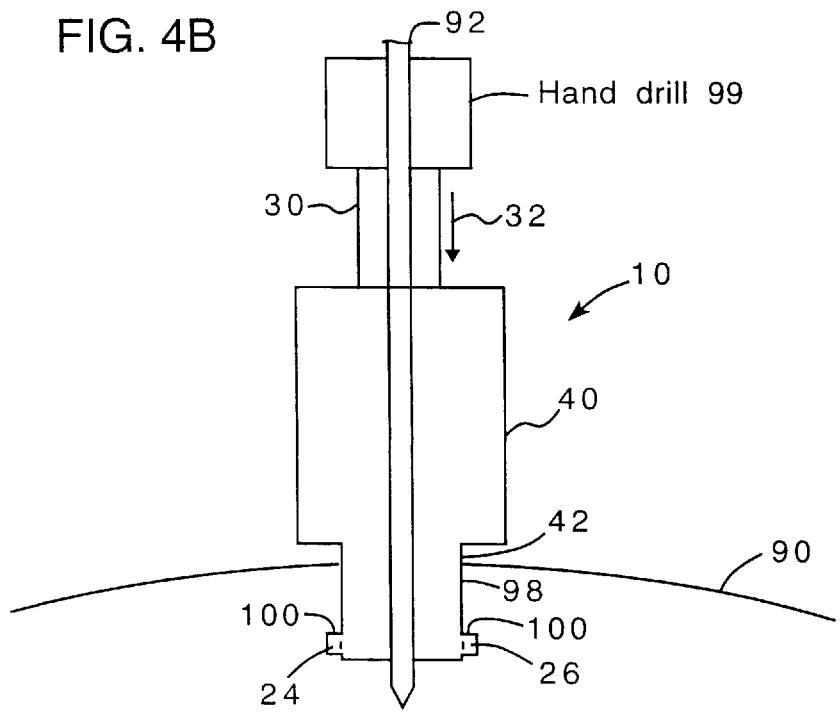

Referring to FIGS. 4–4B, undercutting instrument 10 is used to form an undercut hole in, e.g., bone 90 as follows. First, a K-wire 92 is drilled into bone 90 at the desired location for the undercut hole (FIG. 4). K-wire 92 also serves as a guide for a cannulated, flat bottom drill 94, which is placed over K-wire 92 and drilled into bone 90 to remove an area of articular defect from the surface of the bone (FIG. 4A). Such a defect may be caused by arthritis, in which the articular cartilage surface on the bone is worn away, or by an injury in which the articular cartilage surface is damaged.

Drill 94 is advanced into the subchondral bone to the desired depth (as indicated by markings 96 on the surface of drill 94) to produce a cylindrical hole 98. Note that the maximum depth of hole 98 cannot exceed the length L of distal section 42 (FIG. 2). Hole 98 has a diameter D sized to receive distal section 42 of instrument 10 (e.g., 10 mm). That is, the radius of hole 98 is approximately equal to the common radius R of rounded corners 85 (FIG. 2A) of the distal section 42.

Drill 94 is then removed, and undercutting instrument 10, in the non-cutting position of FIG. 2, is inserted over K-wire 92 into cylindrical hole 98 until the flat end 43 of distal section 42 abuts the bottom of hole 98. K-wire 92 passes through passage 44 in housing 22 and passage 64 in rod 30 (as well as the opening in pin 66). A powered hand drill 99 (through which K-wire 92 also passes) is then attached to the proximal end of rod 30.

The operator pushes hand drill 99 in the direction of arrow 32 to advance rod 30 distally against the force of spring 76 and move arms 12, 14 (and cutting tools 24, 26) from the retracted position of FIG. 2 to the deployed position of FIG. 3. The axial motion of rod 30 required to deploy cutting tools 24, 26 helps ensure that distal section 42 is fully inserted into hole 98 so that the undercut will be properly placed at the bottom of hole 98. Thereafter (or simultaneously), the operator actuates hand drill 99 (arrow 34, FIG. 1) to cause cutting tools 24, 26 to rotate and form an undercut groove 100 around the bottom of hole 98 (FIG. 4B). Debris (e.g., bone and other tissue fragments) produced during cutting is urged between flat surfaces 80, 82 of distal section 42 (FIG. 3A) and the sides of hole 98. Thereafter, the debris may be flushed out of hole 98 by irrigating fluid or withdrawn by suction.

Figure 5A:
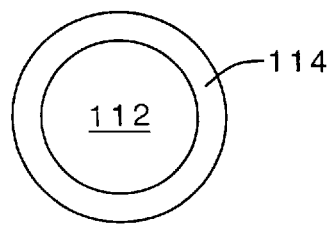
FIGS. 5–5A show a cartilage plug configured to be inserted in the undercut hole formed as shown in FIGS. 4–4B.
Figure 5:
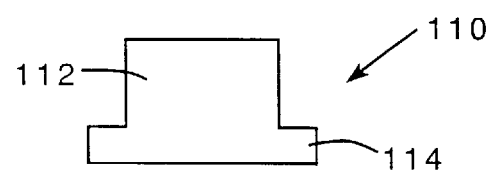

Referring to FIGS. 5 and 5A, the undercut hole formed with drill 94 and undercutting surgical instrument 10 is filled with a plug 110 of hyaline cartilage. Cartilage plug 110 has a cylindrical body 112 sized to fit within the cylindrical portion 98 of the hole and a circular lip 114 configured to fit into undercut groove 100 (FIG. 4B). The overall height of plug 110 should exceed the depth of the undercut hole, for purposes to be described.

Figure 6:
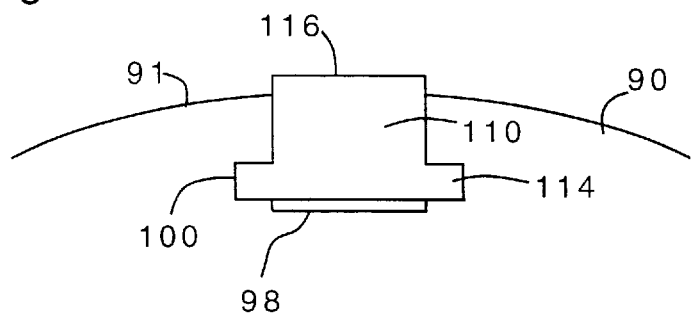
FIGS. 6–6A illustrate placing the cartilage plug of FIGS. 5 and 5A in the undercut hole.
Figure 6A:
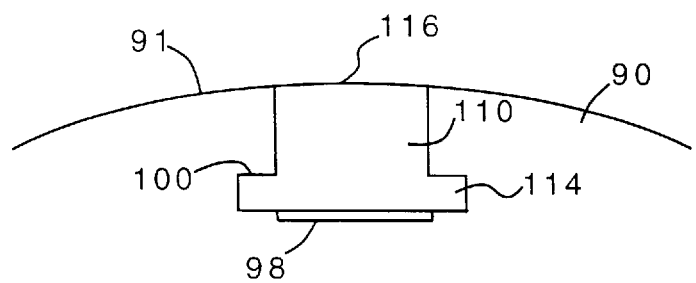

Referring to FIG. 6 and 6A, in use, cartilage plug 110 is placed in the undercut hole with lip 114 located within undercut 100. The resiliency of the cartilage plug enables lip 84 to be pushed through the cylindrical portion 98 of the hole. Because the height of cartilage plug 110 exceeds the depth of the hole, the upper surface 116 of plug 110 protrudes above the articular surface 91 of the cartilage on adjacent bone 90 (FIG. 6). This helps ensure that cartilage plug 110 will not be recessed with respect to articular surface 91, which might otherwise provide a site for defects to form. As a final step, upper surface 116 is shaved down to conform to the profile of the articular surface 91 (FIG. 6A). Alternatively, upper surface 116 can be left protruding from surface 91 (FIG. 6).

Referring to FIGS. 7 and 7A, cartilage plug 110 is formed to the desired size in the operating room during the surgical procedure in which the undercut hole is made. A cylindrical segment of cartilage having a thickness slightly larger than the depth of hole 98 and a diameter equal to that of lip 114 (FIG. 5) is cut from a cartilage sample 120 with a punch 122. (Sample 120 can be, e.g., grown in vitro as a sheet of hyaline cartilage, or harvested.) The cartilage segment is then placed in a shaving device 124 to form plug 110 having the configuration shown in FIGS. 5 and 5A.

The cartilage segment is placed on a support 116, and a cylindrical punch 128 having an inner diameter approximately equal to the outer diameter of plug body 112 (FIG. 5) is lowered into the cartilage segment to a depth approximately equal to the height of cylindrical body 112. The cartilage segment is then pierced by a scalpel 130 at the depth of punch 128. Scalpel 130 is held horizontally by a block 132 which rests on a flat surface of a base 134, and is rotated around support 116 to make an annular cut around the cartilage segment. (Alternatively, the surgeon can make this cut free hand with a scalpel.) The combined cutting action of punch 128 and scalpel 130 removes a sleeve of cartilage from body 112 while leaving lip 114. The completed plug 110 is then removed and inserted into the undercut hole as described above.

Other embodiments are within the scope of the claims.

For example, other mechanisms may be used to move the cutting tools between the retracted and deployed positions. In one alternative, pin 66 can be spring loaded to engage the arms. In another approach, the actuating rod can apply force to arms 12, 14 on opposite sides of the pivot points to respectively deploy and retract the arms.

Other ways of applying the pivoting forces to the arms are also contemplated. For example, rather than the cammed arrangement illustrated in FIGS. 2 and 3, the arms can be pivoted by magnetic force between each arm and the actuating rod. For example, the actuating rod can carry magnets on pin 66 which are positioned adjacent to magnets on the arms when the actuator is moved between the positions of FIGS. 2 and 3. Magnetic attraction (or repulsion) between the magnets would then cause the arms to pivot within the slots. Alternatively, the actuator could deploy the cutting tools by rotational rather than axial motion.

Other cutting tool sizes and configurations may be used. For example, cutting tools may be rounded, triangular, or dovetailed. Also, the undercut (particularly if it is tapered)

may extend over the entire depth of the hole. More or fewer cutting tools than the pair of tools discussed above can be provided.

The surgical instrument can be operated by a manual drill rather than a powered device.

What is claimed is:

1. A surgical instrument comprising
   a housing having a distal section sized to be inserted into a hole in a bone, said housing including a passage therethrough sized to receive a guide wire for placing said distal section at a selected location at the bone,
   an arm pivotally mounted to said housing adjacent to said passage, said arm carrying a cutting tool at said distal section,
   an actuator coupled to said arm to selectively pivot said arm and cause said arm to move said cutting tool between a retracted position and a deployed position, said actuator being coupled to said housing to rotate said distal section with said cutting tool in the deployed position to cause said cutting tool to rotate and form an undercut in the bone hole around the guide wire, and
   a member coupled to said arm to bias said cutting tool to the retracted position.

2. A surgical instrument comprising
   a housing having a distal section sized to be inserted into a hole in a bone, said housing including a passage therethrough sized to receive a guide wire for placing said distal section at a selected location at the bone,
   an arm pivotally mounted to said housing adjacent to said passage, said arm carrying a cutting tool at said distal section, said arm being disposed generally along an axis between a proximal region, at which said arm is pivotally mounted to said housing, and a distal end at which said arm carries said cutting tool, and
   an actuator coupled to said arm to selectively pivot said arm transversely to said axis to cause said arm to move said cutting tool between a retracted position and a deployed position, and said actuator being coupled to said housing to rotate said distal section with said cutting tool in the deployed position to cause said cutting tool to rotate and form an undercut in the bone hole around the guide wire.

3. The instrument of claim 2 wherein said housing includes a slot disposed generally along said axis, said arm being pivotally mounted to said housing within said slot so that said cutting tool is disposed in said slot when in the retracted position and protrudes from said slot when in the deployed position.

4. The instrument of claim 2 wherein said actuator is disposed within said passage and is axially movable with respect to said housing to selectively pivot said arm and cause said arm to move said cutting tool between the retracted position and the deployed position.

5. The instrument of claim 4 wherein said arm includes an axially disposed camming surface positioned to be engaged by said actuator so that the axial movement of said actuator toward said distal section causes said arm to pivot transversely and move said cutting tool between the retracted position and the deployed position.

6. The instrument of claim 5 further comprising a spring disposed in said housing to bias said actuator axially away from said distal section.

7. The instrument of claim 5 wherein said actuator includes a transversely disposed pin that engages said camming surface of said arm.

8. The instrument of claim 7 wherein said housing includes an axially elongated aperture adjacent to said camming surface, said pin extending through said aperture and engaging said camming surface.

9. The instrument of claim 8 wherein engagement of said pin in said aperture rotatably couples said actuator to said housing so that rotation of said actuator is transmitted to rotate said distal section and said cutting tool.

10. The instrument of claim 7 wherein said actuator and said pin include openings which communicate with said passage to receive the guide wire.

11. A surgical instrument comprising
    a housing disposed along a longitudinal axis between a proximal region and a distal section which is sized to be inserted into a hole in a bone, said housing including a passage disposed therethrough along said axis, said passage having an open end at said distal section, said housing further having a plurality of axially extending slots in walls of said housing arranged around said passage, said slots extending between said proximal region and said distal section of said housing,
    a plurality of axially extending arms each of which is disposed in one of said slots, a proximal region of each one of said arms being pivotally mounted to said housing, and a distal end of each one of said arms carrying a cutting tool so that said cutting tools are arranged around the open end of said passage,
    an actuator movably disposed within said passage and coupled to said arms to selectively pivot said arms transversely to said axis and cause said arms to move said cutting tools between a retracted position, in which said cutting tools are disposed in said slots, and a deployed position, in which said cutting tools protrude from said slots,
    said actuator being rotatably coupled to said housing to rotate said distal section with said cutting tools in the deployed position to cause said cutting tools to form an undercut in the bone hole around the open end of said passage.

12. The instrument of claim 11 further comprising a resilient member disposed around said housing for biasing said arms into said slots so that said cutting tools are in the retracted position.

13. The instrument of claim 11 wherein each of said arms includes an axially disposed camming surface, and further comprising
    a plurality of axially elongated apertures in said housing wall, each of said apertures being disposed adjacent to a said camming surface of one of said arms,
    an element mounted on said actuator and configured to extend through said apertures and engage said camming surfaces so that axial movement of said actuator within said passage toward said distal section causes said arms to pivot transversely and move said cutting tools between the retracted position and the deployed position.

14. The instrument of claim 11 wherein engagement of said element in said apertures rotatably couples said actuator to said housing so that rotation of said actuator is transmitted to rotate said distal section and said cutting tools.

15. The instrument of claim 11 further comprising a spring disposed in said housing to bias said actuator axially away from said distal section.

16. A surgical method comprising
    forming a hole having an undercut in bone tissue,
    providing a tissue plug having a portion configured to be received in the undercut, and
    inserting the tissue plug in the hole so that said portion of the plug is disposed in the undercut.

17. The method of claim 16 wherein the forming step includes making the hole in the bone and then forming the undercut in the hole.

18. The method of claim 16 wherein the forming step includes configuring the undercut to be annular, and said providing step includes defining an annular lip on said tissue plug.

19. The method of claim 16 further comprising contouring the tissue plug after the inserting step so that an exposed surface of the tissue plug is flush with surrounding tissue.

20. A method of forming a tissue plug, comprising
providing a sample of the tissue,
cutting a plug from the tissue sample, and
forming a protrusion having a selected configuration on a surface of said plug.

21. The method of claim 20 wherein said cutting includes configuring said plug to be cylindrical, and said forming includes configuring said protrusion to be annular.

* * * * *